US006428989B1

(12) United States Patent
Yukimune et al.

(10) Patent No.: US 6,428,989 B1
(45) Date of Patent: Aug. 6, 2002

(54) METHOD FOR PRODUCING TAXANE-TYPE DITERPENES

(75) Inventors: Yukihito Yukimune; Kouichi Matsubara; Yasuhiro Hara, all of Yamaguchi (JP)

(73) Assignee: Mitsui Chemicals, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 56 days.

(21) Appl. No.: 09/103,508

(22) Filed: Jun. 24, 1998

(30) Foreign Application Priority Data

| Jun. 25, 1997 | (JP) | ............................................. 9-168708 |
| Feb. 10, 1998 | (JP) | .......................................... 10-028525 |
| Mar. 26, 1998 | (JP) | .......................................... 10-079366 |

(51) Int. Cl.⁷ .............................................. C12P 17/02
(52) U.S. Cl. ....................... 435/123; 435/127; 435/420; 435/410; 549/510; 549/511
(58) Field of Search ................................. 435/123, 127, 435/420, 410; 549/510, 511

(56) References Cited

U.S. PATENT DOCUMENTS

| 5,015,744 A | 5/1991 | Holton |
| 5,019,504 A | 5/1991 | Christen et al. |
| 5,344,755 A | 9/1994 | Shearer et al. |
| 5,344,775 A | 9/1994 | Smith |
| 5,407,816 A | 4/1995 | Bringi et al. |
| 5,637,484 A * | 6/1997 | Yukimune .................. 435/123 |

FOREIGN PATENT DOCUMENTS

| EP | 0683232 A1 | 11/1995 |
| EP | 0727492 A2 | 8/1996 |
| JP | 07255495 A | 10/1995 |
| WO | WO 97/44476 | 11/1997 |

OTHER PUBLICATIONS

Kawamura et al., Seibutsu Kogaku Kaishi (1998), 76(1), 3–7.*
Fujita et al., Agric. Biol. Chem., vol. 49, No. 7, pp. 2071–2075 (1985).
Yamada et al., Handbook of Plant Cell Culture, vol. 1, pp. 717–728.
Hara et al., Planta Medica, vol. 55, pp. 151–154 (1989).
1992 World Congress on Cell and tissue Culture, p. 96A.
Y. Fujita et al., Agric. Biol. Chem. vol. 49 (7), 2071–2076 (1985), (Abstract only).

* cited by examiner

Primary Examiner—Irene Marx
(74) Attorney, Agent, or Firm—Birch, Stewart, Kolasch & Birch, LLP (57) ABSTRACT

The present invention discloses a method for producing a taxane-type diterpene(s) by culturing cells of a taxane-type diterpene-producing plant, comprising one or both of the the following steps (a) and (b) to increase the ratio of those cell clusters suitable in size for diterpene production:

(a) at least one operation for removing large cell clusters is conducted with a sieve and/or a filter during preculture of the cells to be supplied to main culture for the production of taxane-type diterpenes or at the time of cell transfer from one preculture to the subsequent preculture;

(b) the cells are cultured under strong agitation conditions.

7 Claims, 1 Drawing Sheet

FIG.1

(Unit : mm)

Curved portions painted black represent pleats

METHOD FOR PRODUCING TAXANE-TYPE DITERPENES

BACKGROUND OF THE INVENTION

1. Field of the Invention

The present invention relates to methods for producing taxane-type diterpenes including taxol which is useful as a therapeutic agent for ovarian cancer, mammary cancer, lung cancer and the like.

2. Description of the Prior Art

Taxol useful as a therapeutic agent for ovarian cancer, mammary cancer, lung cancer, etc. is a taxane-type diterpene isolated and identified from Pacific yew (*Taxus brevifolia* NUTT), a plant belonging to the genus Taxus, the family Taxaceae. This compound has a complex ester group related to its activity. Taxol can be found in any part of the plant body of Pacific yew, and it has been reported that taxol content is the highest in the bark. Currently, taxol is collected from natural or cultured trees. However, Taxus plants are slow-growing plants taking more than 10 years to grow to a height of 20 cm above the ground. Further, peeling the bark results in the death of trees. Therefore, it is difficult to obtain a large quantity of taxol. If it is possible to synthesize taxol and taxane-type diterpenes such as baccatin III (a precursor of taxol) utilizing cell culture, that will be very advantageous for obtaining large quantities of these compounds easily without harvesting trees.

As prior art for taxol production, a semi-synthetic method to produce taxol from baccatin III or 10-deacetylbaccatin III, a precursor in the biosynthesis of taxol, is disclosed in the U.S. Pat. No. 5,015,744 issued to Holton et al. In Europe and the U.S., taxol derived from this semi-synthesis has been approved and used clinically. By using a method of plant cell culture, it is possible to produce raw materials for semi-synthesis, such as baccatin III, which can be utilized for taxol production by the above-described semi-synthetic process.

As a method of taxol production using cultured plant cells, a method has been patented in the U.S. (U.S. Pat. No. 5,019,504) in which taxol is produced from cultured cells of Pacific yew (*Taxus brevifolia* NUTT). According to this method, however, the yield of taxol is 1–3 mg/l which is insufficient for industrial production. Besides, the taxol productivity by cell culture is unstable. Although a primary cell of high productivity can be obtained by selection, it is difficult to maintain the taxol content of the cell through subculture [E. R. M. Wickremesine et al., World Congress on Cell and Tissue Culture (1992)].

Under circumstances, various methods have been tried to improve the productivity of taxol. For example, a method in which cultured cells of *Taxus chinensis* that has a high taxol content are used (U.S. Pat. No. 5,407,816); a method of using a continuous culture process (Japanese Unexamined Patent Publication No. 7-255495); and a method in which methyl jasmonate, an information transmission substance, is added to the medium (Japanese Unexamined Patent Publication No. 8-33490, EP 683232) may be enumerated. However, none of the above-described methods has been put into practical use. Further improvement of the productivity is desired.

Cultured cells of plants will not form single cells but produce cell clusters several ten micrometers to several millimeters in size even when cultured in a liquid medium under agitation because, generally, the cell walls adhering individual cells are firm and solid. In arbor plants such as Taxus plants used in the present invention, intercellular adhesion is particularly strong as a result of the development of secondary cell walls such as lignin.

Recent researches concerning the production of secondary metabolites in cultured plant cells have shown that the secondary metabolites vary depending on the size of these cell clusters [Y. Yamada and Y. Fujita, Handbook of Plant Cell Culture, vol. 1, edited by D. A. Evans et al., Macmillan Publishing Co., New York, pp. 717–728 (1983); Y. Hara et al., Planta Med., 55, pp. 151–154 (1989)]. However, no report has been made on the relation between the particle size of those cell clusters and the productivity of taxane-type diterpenes.

On the other hand, U.S. Pat. No. 5,344,775 discloses the following processes as a method for obtaining small cell clusters of a Taxus plant consisting of 1–10 cells:

(i) providing fragments of callus tissue from Taxus explants containing meristematic tissue physically supported on a support culture medium containing α-napthaleneacetic acid as an auxin, and 6-benzylamino purine as a cytokinin;

(ii) culturing the callus tissue in a liquid medium containing the auxin and the cytokinin to produce a suspension of a plurality of clusters of 1–10 cells having limited intercellular adhesion;

(iii) plating cells removed from the cell suspension onto a surface of a support culture medium containing the auxin and the cytokinin; and (iv) growing the plated cells from step (iii) on the support culture medium form pseudocallus cells, the pseudocallus cells being a loose, amorphous aggregation of cells lacking differentiated vascular or organ tissues and lacking clearly defined meristematic zones, the cell aggregation having poor intercellular adhesion, extreme friability, and falling apart into numerous individual cells and small cell clusters when mechanically disturbed, the pseudocallus cells showing an initial rate of mass doubling in cell growth medium that is greater than the mass doubling of callus tissue of step (i), and exhibiting the property of producing higher levels of taxanes than that produced by callus tissue of step (i).

However, it is extremely difficult to obtain small cell aggregations which consist of 1–10 cells and yet which can grow or produce secondary metabolites. (Cultured cells of Taxus plants are usually 20–30 μm in diameter and, thus, the diameter of a cell aggregation consisting of 10 cells is estimated to be less than 100 μm.) It is impossible to obtain such aggregations unless the medium and culture conditions are elaborately combined as disclosed in the above-mentioned U.S. patent.

In cultured cells of a number of Taxus plants including those cells used by the present inventors, small clusters of 1–10 healthy cells cannot be obtained by merely intensifying the agitation conditions employed in liquid culture. What can be obtained by fractionation using a sieve 100 μm in opening is the debris of aged cells alone which do not have the ability to grow or to produce secondary metabolites.

Therefore, the major point of the separation of small cell clusters as disclosed in the above U.S. patent resides in the preparation of such callus tissue that liberates small cell clusters easily. Thus, this patent is different in basic thought and process from the present invention which defines conditions of shaking and agitation to liberate small cell clusters. In other words, according to the specification of the above U.S. patent, the shaking and agitation conditions of the patent to liberate small clusters consisting of 1–10 healthy cells fall within the range of conventional methods. Unlike the conditions of the present invention, the conditions employed in that U.S. patent are not beyond the range of conditions used in conventional cell culture.

Furthermore, considering actual, industrial culture processes, it is expected in any of the above-described methods to increase the productivity of finally obtained taxane-type diterpenes by employing the so-called two-step culture in which preculture and main culture are performed under different conditions. Preculture is conducted for the purpose of growing cells, and main culture is conducted for the purpose of producing taxane-type diterpenes of interest such as taxol. In the production of taxane-type diterpenes by conventional cell culture methods, improvement of conditions in main culture has been emphasized as seen in the above-mentioned 3 patents relating to the improvement of taxol productivity. For example, an elicitor or information transmission substance is added; or culture process is improved. With respect to preculture, no specific conditions preferable for the improvement of the final productivity of a compound of interest are known.

As roles of preculture, the first one is to increase the growth rate of cells so that cells are supplied to main culture as much as possible. At the same time, preculture is required to increase the latent ability of cells to produce taxane-type diterpenes so that the cells, when transferred, will produce diterpenes efficiently in main culture. However, the importance of preculture conditions from the viewpoint of increasing the cells' latent ability has not been recognized at all as described above.

Generally, as parameters to control or regulate oxygen supply to plant cells or the like in suspension culture, mass transfer volume coefficient ($k_L a$) and dissolved oxygen concentration (DO) can be enumerated, for example. Shaking rate and gas feeding rate cannot be used universally since they are influenced by the shape of the culture vessel and the amount of medium used, though they are easily determined and advantageous in that sense. Thus, they are totally meaningless parameters in terms of cultural engineering. It has been known that the productivity of a product of interest (amount of accumulation/cell) is influenced by $k_L a$ and DO in full-scale culture (Y. Fujita & Y. Hara, Agric. Biol. Chem., 49, pp. 2071–2075 (1985)]. However, the influence of these parameters in preculture has not been examined to date.

OBJECTS AND SUMMARY OF THE INVENTION

It is an object of the invention to improve the productivity of taxane-type diterpenes in methods for producing the same by culturing plant cells.

As a result of intensive and extensive researches toward the solution of the above assignment, the present inventors have found that (i) in culturing taxane-type diterpene-producing plant cells, the use of small cell clusters increases the productivity of taxane-type diterpenes; and (ii) preculturing of taxane-type diterpene-producing plant cells under enriched oxygen supply increases the latent ability of the resultant cells to produce taxane-type diterpenes, improving in turn the productivity of the diterpenes in main culture. Thus, the present invention has been achieved.

The present invention relates to a method for producing a taxane-type diterpene(s) by culturing cells of a taxane-type diterpene-producing plant, comprising one or both of the the following steps (a) and (b) to increase the ratio of those cell clusters suitable in size for diterpene production:

(a) at least one operation for removing large cell clusters is conducted with a sieve and/or a filter during preculture of the cells to be supplied to main culture for the production of a taxane-type diterpene(s) or at the time of cell transfer from one preculture to the subsequent preculture;

(b) the cells are cultured under strong agitation conditions.

The cell cluster suitable in size for diterpene production has a mean diameter ranging from 0.12 mm to 1.6 mm, preferably from 0.12 mm to 1.0 mm, the mean diameter being represented by an intermediate value between the major axis and the minor axis of the cell cluster.

Preferably, the ratio of the cell clusters suitable in size for diterpene production is increased to 65% or more, especially 80% or more, relative to the gross fresh weight of the cells.

The present invention also relates to a method for producing a taxane-type diterpene(s) by culturing cells of a taxane-type diterpene-producing plant, comprising:

preculturing the cells in a liquid medium under oxygen supply conditions wherein the mass transfer volume coefficient ($k_L a$) of oxygen against the liquid medium is $10\ h^{-1}$ or more;

supplying the resultant cells to main culture for the production of a taxane-type diterpene(s); and recovering the taxane-type diterpene(s) from the resultant culture.

Further, the present invention relates to a method for producing a taxane-type diterpene(s) by culturing cells of a taxane-type diterpene-producing plant, comprising:

preculturing the cells in a liquid medium under conditions wherein the dissolved oxygen concentration (DO) of the liquid medium is retained at 30% or more of the saturated oxygen concentration at the temperature employed in the culture;

supplying the resultant cells to full-scale culture to produce a taxane-type diterpene(s); and recovering the taxane-type diterpene(s) from the resultant culture.

DETAILED DESCRIPTION OF THE INVENTION

Hereinbelow, the present invention will be described in detail.

Examples of taxane-type diterpene-producing plants to be used in the production method of the invention include Taxus plants such as European yew (*Taxus baccata* LINN), Japanese yew (*T. cuspidata* SIEB. et ZUCC), Kyaraboku (*T. cuspidata* SIEB. ET ZUCC var. nana REHDER), Pacific yew (*T. brevifolia* NUTT), Canadian yew (*T. canadensis* MARSH), Chinese yew (*T. chinensis*), Himalayan yew (*T. wallichiana* ZUCC) and *T. media*. Among all, European yew and *T. media* are particularly preferable.

First, an explant taken from a part of Taxus plants such as a root, growing point, leaf, stem, seed or the like is sterilized, placed on Woody Plant Medium (hereinafter referred to as "WP medium") solidified with gelan gum, and kept at 10–35° C. for 14–60 days so that a part of the tissue piece is changed to a callus. Subculturing the thus obtained callus accelerate the growth rate gradually to yield a stabilized callus. The term "stabilized callus" refers to a callus which remains in a callus state during culture without showing differentiation into shoots or roots and the cells of which have a uniform growth rate.

Such a stabilized callus is transferred to a liquid medium suitable for growth (e.g., liquid WP medium). Then, the growth rate is further accelerated (preculture at this stage is particularly referred to as "growth culture").

In one embodiment of the invention, one or both of the following steps are carried out in order to increase from these stabilized cells those cell clusters suitable for the production of taxane-type diterpenes.

In the first step, large cell clusters are removed by sieving cultured cells. This removal operation may be conducted with a filter instead of a sieve or with a combination of a sieve and a filter. The opening of the sieve is not particularly limited as long as the sieve can remove large cell clusters. Considering efficiency in improving the productivity of the product of interest, the opening is preferably 1410 $\mu$m or less, more preferably 840 $\mu$m or less.

Since clusters of cultured cells of a Taxus plant are not spherical, those cell clusters having a minor axis shorter than the above-mentioned opening can pass through each of the above sieves. The mean diameter of the cell cluster capable of passing through each sieve which is represented by an intermediate value of the major axis and the minor axis of the cell cluster is 1.6 mm or less when the opening is 1410 $\mu$m and 1.0 mm or less when the opening is 840 $\mu$m. Those cell clusters which can pass through a sieve 100 $\mu$m in opening and which have a mean diameter of 0.12 mm or less may be either removed from the cell population or left therein, because both their ability to grow and their ability to produce taxane-type diterpenes are remarkably reduced.

The time to sieve cultured cells may be either during preculture or the time of cell transfer from one preculture to the subsequent preculture. In view of operational efficiency and economy, the time of cell transfer is preferable. It is preferred that an operation to remove large cell clusters be conducted at least once during culture at the 2nd to 10th culture prior to main culture for the production of taxane-type diterpenes and/or at the time of cell transfer carried out at the beginning of each of the 2nd to 10th culture. Although it is possible to conduct a sieving operation at the time of cell transfer from preculture to main culture, sieving at this point is disadvantageous in view of culture cost and waste material disposal cost because the amount of cells is large in the preculture immediately before main culture; the possibility of contamination by microorganisms during the sieving operation is high; and the amount of large cell clusters to be discarded is also large.

WO 95/14103 (EP 683232) discloses a method in which cells are fractionated by particle size at the time of cell transfer from preculture to main culture. However, the fractionation is conducted for the purpose of increasing the accuracy of experiments, and the method of this reference is completely different from the method used in the present invention in thought and operation. That is, since the effect of the invention of increasing the ratio of those cell clusters suitable for taxane-type diterpene production by sieving usually lasts from about 2 to about 10 generations without conducting a similar operation at the time of cell transfer subsequent to the sieving operation, it is not necessary to conduct that operation again at the time of cell transfer from preculture to main culture.

When the sieving of cultured cells is conducted during culture, the cells may be once taken out from the culture vessel for sieving. Alternatively, a sieve or a filter may be incorporated in a culture apparatus so that large cell clusters can be removed automatically. It is also possible to conduct the above sieving operation regularly when cells are transferred to a fresh medium to thereby obtain a group of stable small cell clusters.

The term "preculture" used herein refers to culture which is conducted mainly for the purpose of growing seed cells to be supplied to main culture and which is to increase the culture scale by stages according to the increase in cell quantity. For the production of taxane-type diterpenes, usually, preculture is conducted 2–10 times. The term "main culture" used herein refers to culture which is conducted for the purpose of producing the product of interest, taxane-type diterpenes, finally.

In the second step, cells are cultured under conditions to effect strong agitation (hereinafter referred to as "strong agitation conditions") which would not damage individual cells in order to crush large cell clusters to thereby yield small cell clusters. The term "strong agitation conditions" used herein refers to those conditions under which cell clusters are crushed so that the ratio of small cell clusters having a mean diameter ranging usually from 0.12 mm to 1.6 mm, preferably from 0.12 mm to 1.0 mm becomes usually 65% or more, preferable 80% or more relative to the gross fresh weight of the cells.

Such agitation conditions can be achieved by increasing the rotation speed of impellers or altering the shape thereof, or by installing baffles in the culture vessel. Culture under such agitation conditions may be conducted in either main culture for the production of taxane-type diterpenes or preculture. During the culture period, agitation intensity may be increased for a specific period or throughout the culture period.

In order to achieve the above agitation conditions by increasing the rotation speed of impellers, paddle-type impellers whose diameter is ½ of the inner diameter of the culture vessel and whose height is ¼ of the depth of the culture liquid may be used, for example, at a speed of 30–180 rpm, preferably 40–120 rpm, when cells have normal intercellular adhesion intensity.

In order to achieve the above agitation conditions by altering the shape of impellers, for example, hollow paddle-type, screw-type or turbine-type impellers are used.

In order to achieve the above agitation conditions by installing baffles in the culture vessel, the stretching distance from the inner wall surface of the culture vessel to the end of the baffle is increased and/or the number of baffles installed is increased.

The cell clusters thus obtained are supplied to main culture conducted for the purpose of taxane-type diterpene production.

In another embodiment of the invention, preculture is performed to obtain from the stabilized cells described above seed cells with increased latent ability to produce taxane-type diterpenes. The resultant seed cells are supplied to main culture to produce taxane-type diterpenes.

In the present invention, the term "latent ability to produce" means the ability of cells to produce larger amounts of taxane-type diterpenes when they are transferred to a new medium. In other words, this term means capacity as seed cells (inoculum).

The culture to obtain seed cells with increased latent ability to produce taxane-type diterpenes is conducted under conditions where enriched oxygen is supplied.

Specifically, the enriched oxygen supply can be achieved by setting the mass transfer volume coefficient (hereinafter referred to as "$k_L a$") of oxygen against the liquid medium at 10 $h^{-1}$ or more, preferably in the range from 15 to 50 $h^{-1}$.

The capacity of seed cells can be improved even under conditions where $k_L a$ is greater than 50 h$^{-1}$. However, practically, it is not preferable to increase $k_L a$ by increasing the aeration speed and/or the agitation speed since there will occur problems such as the blowing of cells up to the surface of the culture solution and damage to cells. In order to determine the value of $k_L a$, the following method may be used, for example. Briefly, $CuSO_4$ is added to a liquid medium that is the same as used in the invention except that cells are not contained, under the same conditions in temperature, agitation, etc. as employed in the culture method of the invention. Then, oxygen-containing gas with a specific oxygen concentration is fed thereinto to determine the saturated dissolved oxygen concentration (Cs). Subsequently, an appropriate amount of an aqueous $Na_2SO_3$ solution is added or a non-oxygen gas such as nitrogen gas is fed there into to adjust the dissolved oxygen concentration at 0–1 ppm. (In case that the non-oxygen gas is used, $CuSO_4$ does not need to be added to the liquid medium.) Thereafter, the above oxygen-containing gas is fed again at a specific aeration speed to increase the dissolved oxygen concentration. Dissolved oxygen concentrations $C_1$ and $C_2$ at the time points $t_1$ and $t_2$, respectively, after the re-feeding of the oxygen-containing gas are determined. Then, $k_L a$ under certain culture conditions can be determined by the following formula (using those data in which both $C_1$ and $C_2$ are in the range from 3 to 5 ppm):

$$ln+e, fra\ Cs-C_1/Cs-C_2+ee = k_L a(t_2-t_1)$$

Generally, the value of $k_L a$ depends on the aeration speed, agitation speed, and the like.

Methods for controlling $k_L a$ include increasing or decreasing the culture solution, alteration of the shaking method (rotation type or piston type), increasing or decreasing the shaking speed, and the like for flask culture; and alteration of the shape of the tank, increasing or decreasing of the amount of aeration, alteration of the location of the sparger or the diameter of the gas jet, installation of baffles, alteration of the shape of impellers and the rotation speed, and the like for tank culture. Of these, increasing or decreasing the amount of aeration and alteration of the rotation speed of impellers are preferable as methods for controlling $k_L a$ for tank culture.

Conventionally employed $k_L a$ values are less than 10 h$^{-1}$ in both flask culture and tank culture. Although values exceeding 10 h$^{-1}$ are employed exceptionally, they are employed in main culture. It is not known that the effect which is achieved by setting the $k_L a$ of preculture in the above-mentioned range appears later in main culture. Additionally, it is preferable to set the $k_L a$ in preculture higher than that in main culture.

The second condition for enriched oxygen supply is achieved by maintaining the saturated oxygen concentration (hereinafter referred to as "DO") of the liquid medium in which cells are cultured at 30–90%, preferably 50–75%. Since DO is influenced by the respiration rate of cells as well as $k_L a$, it is impossible to control DO simply by aeration speed and agitation speed alone. However, it can be controlled by automatically increasing or decreasing the aeration speed or increasing or decreasing the oxygen concentration in the gas for aeration, while monitoring DO in the culture solution with an oxygen electrode or the like.

In the present invention, the preculture conducted for improving the capacity of seed cells by setting $k_L a$ and/or DO in the above-described range(s) manifests the effect in main culture if conducted usually up to 10 generations before main culture. The effect of such preculture is stronger when conducted closer to main culture. It is most appropriate to conduct such preculture the culture immediately before main culture.

The taxane-type diterpene is not particularly limited as long as it has a taxane skeleton. Specific examples include taxol, 10-deacetyltaxol, 7-epitaxol, baccatin III, 10-deacetylbaccatin III, 7-epibaccatin III, cephalomannine, 10-deacetylcephalomannine, 7-epicephalomannine, baccatin VI, taxane 1a, xylosyl cephalomannine, xylosyl taxol, taxol C, 10-deacetyltaxol C, taxisine I, taxisine II, taxine I, taxine II and taxagifine.

Examples of the medium to be used for culturing cells in the present invention include those known media which have been conventionally used for plant cell culture, such as Murashige & Skoog medium (1962), Linsmaier Skoog medium (1965), Woody Plant Medium (1981), Gamborg's B-5 medium, M-9 medium of Fujita et al.

Phytohormones and, if necessary, carbon sources, inorganic components, vitamins, amino acids and the like may be added to these media.

As the carbon sources, disaccharides such as sucrose, maltose and lactose; monosaccharides such as glucose, fructose and galactose; starch; or a mixture of two or more of these sugar sources at an appropriate ratio may be used.

As the inorganic components, specific examples include phosphorus, nitrogen, potassium, calcium, magnesium, sulfur, iron, manganese, zinc, boron, copper, molybdenum, chlorine, sodium, iodine and cobalt. These components may be added in the form of such compounds as potassium nitrate, sodium nitrate, calcium nitrate, potassium chloride, potassium monohydrogenphosphate, potassium dihydrogenphosphate, calcium chloride, magnesium sulfate, sodium sulfate, ferrous sulfate, ferric sulfate, manganese sulfate, zinc sulfate, boric acid, copper sulfate, sodium molybdate, molybdenum trioxide, potassium iodide, cobalt chloride and the like.

As the phytohormones, auxin such as indoleacetic acid (IAA), naphthaleneacetic acid (NAA) and 2,4-dichlorophenoxy acetic acid (2,4-D); and cytokinin such as kinetin, zeatin and dihydrozeatin may be used, for example.

As the vitamins, biotin, thiamin (vitamin B1), pyridoxine (vitamin B6), pantothenic acid, inositol, nicotinic acid and the like may be used.

As the amino acids, glycine, phenylalanine, leucine, glutamine, cysteine and the like may be added.

Generally, the inorganic components are used at a concentration of about 0.1 M–100 mM; the carbon sources at a concentration of about 1–30 g/liter; the phytohormones at a concentration of about 0.01–10 M; and the vitamins and amino acids at concentrations of about 0.1–100 mg/liter, respectively.

In the cell culture of the present invention, a tissue piece or cells from a root, growing point, leaf, stem, seed, pollen, anther, calyx, etc. of the above-mentioned plant, or cultured cells obtained by culturing such tissue piece or cells in the above-mentioned medium or a conventional medium may be used.

Taxane-type diterpenes can be isolated from the thus obtained cultured tissues, cultured cells and/or medium by extraction with an organic solvent such as methanol. Alternatively, it is also possible to recover taxane-type diterpenes continuously by allowing an appropriate adsorbent and organic solvent to co-exist in the medium.

In the present invention, the productivity of taxane-type diterpenes can be improved further by adding to the medium, as a production promoting agent, a jasmonic acid or a jasmonic acid derivative such as methyl jasmonate as disclosed in EP 683232; an imino- or amino-derivative of jasmonic acids as disclosed in EP 727492; coronatine or a coronatine derivative such as coronafacic acid as disclosed in EP 727492; a compound containing a heavy metal and/or heavy metal ion as disclosed in EP 683232; amines as disclosed in EP 683232; or a cyclic polysaccharide such as cyclodextrin as disclosed in EP 727492.

As a culture temperature to be employed in the cell culture of the present invention, usually about 10–35° C. is used. Particularly preferable is 23–28° C. because of a great growth rate achieved at these temperatures. As a culture period, 7–42 days are preferable.

When a liquid medium is used in the culture method of the present invention, cultured cells are separated from the medium by decantation or filtration after completion of the culture. Then, the taxane-type diterpene(s) of interest can be separated from the cells and/or the medium by, for example, extraction with an organic solvent.

As a method of increasing the effect of the present invention further, use of the method of the present invention together with the method disclosed in EP 683232 may be given. In the latter method, cells are fractionated into a plurality of layers according to their specific gravities, and cells contained at least one of the layers are cultured.

It is also possible to improve the productivity further by employing in the present invention the main culture conditions disclosed in EP 683232, i.e., culture is conducted by controlling the oxygen concentration in a gas phase in a culture vessel to less than the oxygen concentration in the atmosphere from the initial stage of the culture, or by controlling the dissolved oxygen concentration in a fluid medium which is in contact with the tissues and/or the cells to less than the saturated dissolved oxygen concentration at that temperature, which the cells were cultured, from the initial stage of the culture.

EFFECT OF THE INVENTION

According to the present invention, it becomes possible to obtain large quantities of taxane-type diterpenes easily by culturing cells of a taxane-type diterpene-producing plant.

PREFERRED EMBODIMENTS OF THE INVENTION

Hereinbelow, the present invention will be described more specifically with reference to the following Examples and Comparative Examples. However, the scope of the present invention is not limited to these Examples.

EXAMPLE 1

Effect of the Shaking Speed in Preculture Upon Fractionation of Cell Clusters with Sieves (1) Preculture An embryo was isolated aseptically from a seed of *Taxus media* sterilized with 2% antiformin solution or 70% ethanol solution. A part of the embryo was placed on solid WP medium (containing 0.25% by weight of gelan gum) supplemented with α-naphthaleneacetic acid at a concentration of $10^{-5}$ M and autoclave-sterilized. Static culture was carried out in a dark place at 25° C. to obtain a callus. Subsequently, 4 g (fresh weight) of this callus was transferred into a 300 ml flask containing 100 ml of liquid WP medium supplemented with α-naphthaleneacetic acid at the same concentration as described above and autoclave-sterilized (hereinafter referred to as the "standard medium"), and gyratory shake culture was carried out on a rotary shaker (amplification: 25 mm; 100 rpm). The callus was subcultured every 14 days 5 times in total to accelerate the growth rate. The thus obtained cells are designated "standard cells".

The standard cells were transferred into a flask under the same conditions as described above, and cultured on a rotary shaker of the same type for 14 days at a shaking speed of 170 rpm.

(2) Sieving

The resultant cells were fractionated successively according to the the size of cell clusters using stainless sieves 1410 μm, 840 μm and 500 μm in opening. Then, the fresh weight ratios of individual fractions were determined.

On the other hand, for the purpose of comparison, the standard cells were subjected to the same sieving procedure without conducting the shake culture at 170 rpm to fractionate by the size of cell clusters. Then, the fresh weight ratios of individual fractions were determined. The results from both sieving procedures are shown in Table 1.

TABLE 1

| | Particle Size Distribution (%) in Cells Cultured at 170 rpm and Cells Cultured at 100 rpm | |
|---|---|---|
| Fraction | Cells cultured at a shaking speed of 170 rpm | Cells cultured at a shaking speed of 100 rpm |
| >1410 μm | 6.1 | 38.0 |
| 840–1410 μm | 15.1 | 22.7 |
| 500–840 μm | 31.0 | 28.3 |
| <500 μm | 47.8 | 11.0 |

EXAMPLE 2

Taxol Productivity of Cells Derived from Each Particle Size Fraction

Two grams (fresh weight) each of the 4 fractions obtained in Example 1 was transferred into a 100 ml Erlenmeyer flask containing 20 ml of the standard medium containing 100 μM methyl jasmonate which is a promoting agent for taxane-type diterpene production. Then, shaking culture was carried out on a rotary shaker of the same type as described above set at 100 rpm in a dark place at 25° C. for 14 days (main culture).

After completion of the culture, cells were harvested by filtration and freeze-dried. The dry weight of the cells was measured to determine the weight of cultured cells per liter of the liquid medium. Taxane-type diterpenes were extracted from the dried callus with methanol or the like, and quantitatively determined by comparing with standard products using high performance liquid chromatography, to thereby determine the yield of taxol. Also, taxane-type diterpenes were extracted from the culture filtrate with dichloromethane, followed by the same quantitative determination as described above. The results are shown in Table 2.

TABLE 2

| | Taxol Productivity of Cells Derived from Each Particle Size Fraction | |
|---|---|---|
| Fraction | Dry cell yield (g/l) | Yield of taxol (mg/l) |
| >1410 μm | 18.5 | 20 |
| 840–1410 μm | 17.4 | 24 |
| 500-840 μm | 21.7 | 49 |
| <500 μm | 18.0 | 82 |

TABLE 2-continued

Taxol Productivity of Cells
Derived from Each Particle Size Fraction

| Fraction | Dry cell yield (g/l) | Yield of taxol (mg/l) |
|---|---|---|

*Yield of taxol was calculated from the gross production (i.e., taxol harvested from cells + taxol from medium).

Table 2 shows that the smaller the mesh size of a stainless steel sieve is, the greater the yield of taxol in those cells fractionated with the sieve is.

EXAMPLE 3

Effect of the Shaking Speed in Preculture Upon Taxol Production (1) Preculture

Four grams (fresh weight) of the standard cells described in Example was transferred into a 300 ml Erlenmeyer flask containing 100 ml of the standard medium, and shaking culture was carried out on a rotary shaker of the same type as described above set at 170 rpm in a dark place at 25° C. for 14 days.

(2) Main culture

The resultant cells were separated from the liquid medium by filtration. Then, 2 g (fresh weight) of the cells was transferred into 100 ml Erlenmeyer flask containing 20 ml of the standard medium containing 100 $\mu$M methyl jasmonate. Shaking culture was carried out on a rotary shaker of the same type as described above set at 100 rpm in a dark place at 25° C. for 14 days. The resultant cells and medium were treated in the same manner as described in Example 2, followed by determination of the dry cell yield and the yield of taxol.

On the other hand, the same operations were carried out except that the shaking speed of the rotary shaker in preculture was set at 100 rpm and 80 rpm, followed by determination of the dry cell yield and the yield of taxol.

Figure 1:
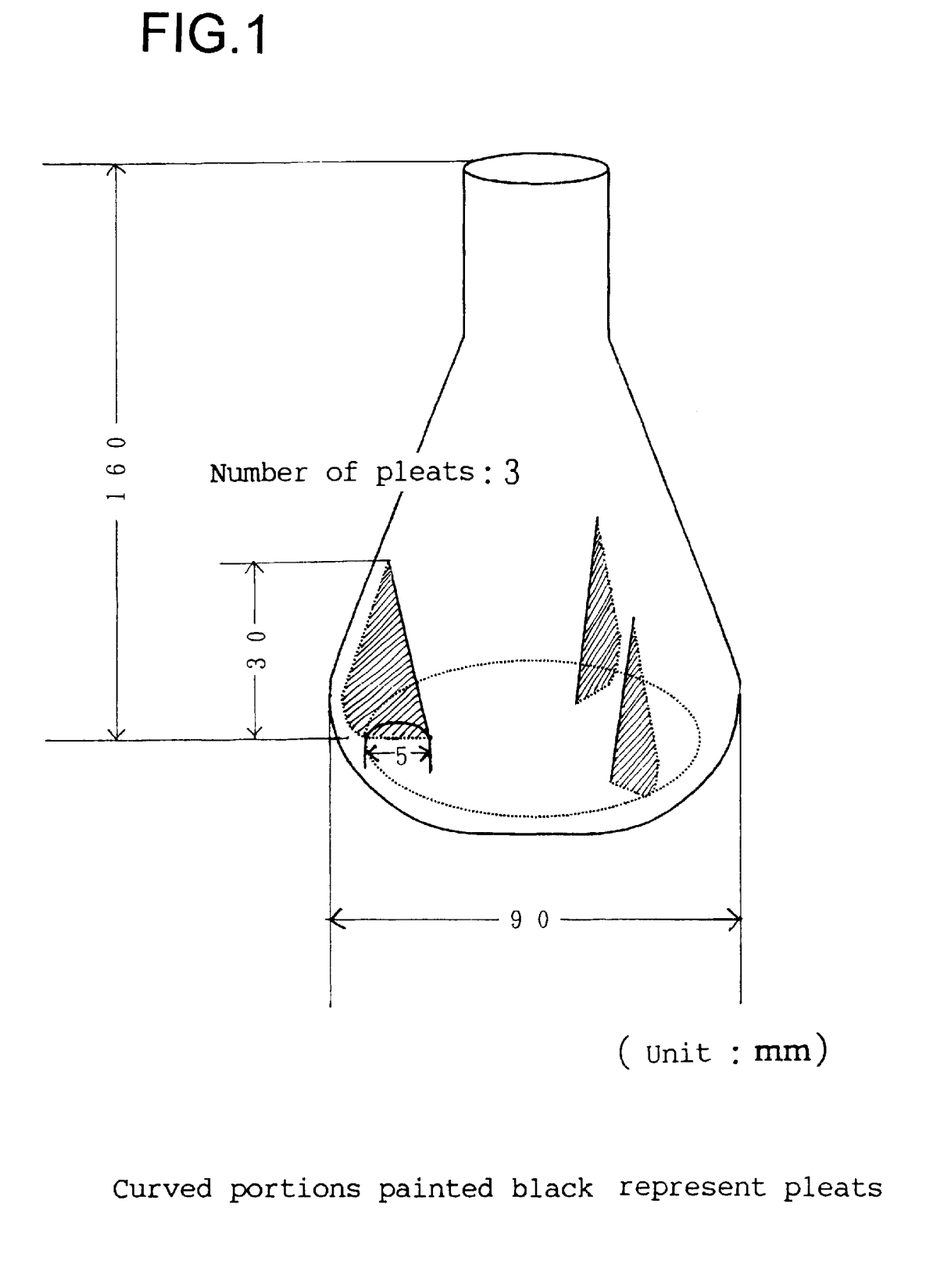
FIG. 1 is a diagram showing a flask provided with pleats at the bottom which serve as baffles.

Further, the same operations were carried out except that the flask used in preculture was provided with pleats which serve as baffles in order to increase the agitation intensity (see FIG. 1). Then, the dry cell yield and the yield of taxol were determined. The results are summarized in Table 3.

TABLE 3

| | Shaking speed in preculture (rpm) | | | |
|---|---|---|---|---|
| | 80 | 100 | 170 | Flask with pleats |
| Dry cell yield (g/l) | 20 | 19 | 23 | 20 |
| Taxol (mg/l) | 21 | 72 | 116 | 140 |

Table 3 shows that the yield of taxol increases as the shaking speed in preculture increases.

EXAMPLE 4

Effect of the Agitation Speed in Main Culture Upon Taxol Production and Effect thereof Upon the Particle Size of Cell Clusters One liter of the standard medium containing 100 $\mu$M methyl jasmonate and 100 g (fresh weight) of the standard cells were transferred into a jar fermentor provided with modified paddle-type impellers set at an agitation speed of 40 rpm, 60 rpm or 80 rpm. The cells were cultured while feeding 1% $CO_2$-containing air at a speed of 0.1 vvm in the dark at 25° C. for 14 days. A part of the resultant cells, and the medium were treated in the same manner as described in Example 2 to determine the dry cell yield and the yield of taxol. The remaining cells were sieved with a sieve 840 $\mu$m in opening, and the ratio of small particle size cells passing through this sieve was determined. The results are shown in Table 4.

TABLE 4

| | Agitation speed (rpm) | | |
|---|---|---|---|
| | 40 | 60 | 80 |
| Weight ratio (%) of small cell clusters* in gross fresh weight of cells | 51 | 68 | 81 |
| Dry cell yield (g/l) | 19 | 20 | 19 |
| Taxol (mg/l) | 46 | 61 | 75 |

*Cells passing through a sieve 840 $\mu$m in opening

Table 4 shows that the yield of taxol increases as the agitation speed in main culture increases. Besides, in those cells cultured with a higher agitation speed, the ratio of small cell clusters in the gross fresh weight of cells increases.

EXAMPLE 5

Effect of Cell Cluster Fractionation with a Sieve Upon Taxol Production

From the standard cells described in Example 1, cell clusters passing through a stainless steel sieve 1410 $\mu$m or 840 $\mu$m in opening were removed. Then, the remaining cells were separated from the liquid medium by filtration. Four gram (fresh weight) of the resultant cells was transferred into a 300 ml Erlenmeyer flask containing 100 ml of standard medium, and cultured under shaking on a rotary shaker of the same type as described above set at 100 rpm in a dark place at 25° C. for 14 days. The entire cells obtained were separated from the liquid medium by filtration. Two grams of the resultant cells was transferred into a 100 ml Erlenmeyer flask containing 20 ml of the standard medium containing 100 $\mu$M methyl jasmonate, and cultured under shaking on a rotary shaker of the same type as described above set at 100 rpm in a dark place at 25° C. for 14 days. The resultant cells and the medium were treated in the same manner as described in Example 2 to determine the dry cell yield and the yield of taxol. The results are shown in Table 5.

On the other hand, the standard cells were treated in the same manner as described above except that removal of large cell clusters with a sieve was not carried out. Then, the dry cell yield and the yield of taxol were determined. The results are also shown in Table 5.

TABLE 5

Taxol Productivity of Each Cell Cluster Group

| Cell cluster group | Dry cell yield (g/l) | Taxol (mg/l) |
|---|---|---|
| No fractionation | 19 | 60 |
| <1410 $\mu$m | 20 | 97 |
| <840 $\mu$m | 21 | 122 |

*Yield of taxol was calculated from the gross production (i.e., taxol harvested from cells + taxol from medium).

Table 5 shows that cells fractionated with a sieve of smaller opening at the time of cell transfer in preculture produce more taxol.

EXAMPLE 6

Particle Size Distribution in Cells Fractionated with Sieves 500 μm or Less in Opening, and Taxol Productivity in the Resultant Fractions The standard cells obtained in Example 1 were sieved in the same manner as in Example 1 except that sieves 500 μm, 250 μm and 100 μm in opening were used. For each of the resultant fractions, the ratio of cell fresh weight was determined. The results are shown in Table 6.

TABLE 6

Particle Size Distribution (%) in
Cells Cultured at 170 rpm and Cells Cultured at 100 rpm

| Fraction | Cells cultured at a shaking speed of 170 rpm | Cells cultured at a shaking speed of 100 rpm |
|---|---|---|
| >500 μm | 56.1 | 87.1 |
| 250–500 μm | 29.2 | 10.5 |
| 100–250 μm | 13.0 | 2.1 |
| <100 μm | 1.7 | 0.3 |

Those cells passed through the 100 μm sieve were examined with a microscope. As a result, it was found that, regardless of the shaking speed, all of them are populations of aged cells changed into brown or the debris thereof though a very small number of clusters consisting of 1–10 cells were observed. These cells were re-cultured in the same manner as in Example 2, but new cell growth or production of taxane-type diterpenes was not observed at all.

Thus, although the fraction fractionated with the 500 μm sieve was confirmed to have an improved taxol productivity in Example 2, those cells contained therein and passing through the 100 μm sieve were recognized to be unsuitable for the production of taxane-type diterpenes of the present invention.

EXAMPLE 7

Effect of $k_L a$ in Preculture (1) Preculture

An embryo was isolated aseptically from a seed of *Taxus media* sterilized with 2% antiformin solution or 70% ethanol solution. A part of the embryo was placed on solid WP medium (containing 0.25% by weight of gelan gum) supplemented with α-naphthaleneacetic acid at a concentration of $10^{-6}$ M and autoclave-sterilized. Static culture was carried out in the dark at 25° C. to obtain callus. Subsequently, 4 g (fresh weight) of this callus was transferred into a 300 ml flask containing 100 ml of liquid WP medium supplemented with α-naphthaleneacetic acid at the same concentration as described above and autoclave-sterilized, and gyratory shake culture was carried out on a rotary shaker (amplification: 25 mm; 100 rpm). The callus was subcultured every 14 days to accelerate the growth rate (the thus obtained cells are designated "standard cells"). Hereinbelow, the conditions of shaking culture are the same as described above unless otherwise noted.

The resultant standard cells were transferred into a 100 ml Erlenmeyer flask containing 15 ml or 20 ml of liquid WP medium to give a cell density of 40 mg (fresh weight)/ml, and cultured for 14 days (preculture).

The $k_L a$ value for each of the above volumes of the medium was calculated by the method described previously. As a result, $k_L a$ values were 21 $h^{-1}$ when the medium was 15 ml and 16 $h^{-1}$ when the medium was 20 ml.

The cells were recovered from each flask by vacuum filtration. A part thereof was supplied to main culture as seed cells. The remaining cells were freeze-dried. The dry weight of the cells was measured to determine the weight of cultured cells per liter of the liquid medium, followed by calculation of the cell yield.

On the other hand, a part of the resultant cells were freeze-dried, and then taxane-type diterpenes were extracted therefrom with methanol or the like. The diterpenes were quantitatively determined by comparing with standard products using high performance liquid chromatography, to thereby determine the yields of taxol and baccatin III. Also, taxane-type diterpenes were extracted from the medium with dichloromethane, followed by the same quantitative determination. The resultant amounts were added to the amounts of taxane-type diterpenes extracted from the cells. The results are shown in Table. 7.

(2) Main Culture

Main culture was carried out by the following procedures. First, to each well of Nunc Multidish 6 (Nunc Co.), 4 ml of liquid WP medium containing 100 μM methyl jasmonate (JA-Me) and 500 mg (fresh weight) of the above-mentioned seed cells were added and cultured under shaking for 14 days in the same manner as described above (main culture). As a control, cells were cultured in the same manner in JA-Me free liquid WP medium.

After completion of the culture, the medium was recovered with a pipette. The cells remaining in wells were freeze-dried. The dry weight of the cells was measured to determine the weight of cultured cells grown per liter of the liquid medium, followed by calculation of the cell yield. Also, taxane-type diterpenes were extracted and subjected to quantitative determination in the same manner as described above. The results are shown in Table 8. The $k_L a$ in the main culture was 5 $h^{-1}$.

COMPARATIVE EXAMPLE 1

The same operations as in Example 7 were carried out except that the volume of the medium in a 100 ml flask was 30 ml or 40 ml when the standard cells were first transferred in the preculture. The results are shown in Tables 7 and 8. The $k_L a$ values as determined by the method described previously were 9 $h^{-1}$ when the medium was 30 ml and 6 $h^{-1}$ when the medium was 40 ml.

TABLE 7

(After preculture)

| Volume of the medium (ml/flask) | $k_L a$ ($h^{-1}$) | Cell yield (g/l) | Taxol (mg/l) | Baccatin III (mg/l) |
|---|---|---|---|---|
| 15 (Example 7) | 21 | 11 | 9 | 3 |
| 20 (Example 7) | 16 | 11 | 7 | 2 |
| 30 (Com. Example 1) | 9 | 12 | 11 | 3 |
| 40 (Com. Example 1) | 6 | 11 | 3 | 1 |

TABLE 8

(After full-scale culture)

| Volume of the medium | Cell yield (g/l) | | Taxol (mg/l) | | Baccatin III (mg/l) | |
|---|---|---|---|---|---|---|
| (ml/flask) | +JA-Me | –JA-Me | +JA-Me | –JA-Me | +JA-Me | –JA-Me |
| 15 (Example 7) | 25 | 27 | 280 | 93 | 148 | 31 |
| 20 (Example 7) | 24 | 26 | 251 | 88 | 138 | 27 |
| 30 (Com. Example 1) | 24 | 26 | 146 | 36 | 43 | 9 |

TABLE 8-continued (After full-scale culture)

| Volume of the medium | Cell yield (g/l) | | Taxol (mg/l) | | Baccatin III (mg/l) | |
|---|---|---|---|---|---|---|
| (ml/flask) | +JA-Me | −JA-Me | +JA-Me | −JA-Me | +JA-Me | −JA-Me |
| 40 (Com. Example 1) | 26 | 28 | 47 | 25 | 40 | 4 |

As shown in Table 7, no effect of $k_L a$ in preculture upon the amount of cells obtained at the end of preculture (cell yield) or the productivity of taxane-type diterpenes (yields of taxol and baccatin III) was recognized.

On the other hand, as shown in Table 8, a remarkable effect of $k_L a$ in preculture upon the productivity of taxane-type diterpenes (yields of taxol and baccatin III) was recognized, though no effect was recognized upon the amount of cells obtained at the end of full-scale culture (cell yield). That is, the productivity of taxane-type diterpenes (yields of taxol and baccatin III) was remarkably increased in Example 7. Besides, the productivity was further increased in the medium containing JA-Me.

EXAMPLE 8

EFFECT of $k_L a$ in Preculture

To a jar fermentor provided with modified paddle-type impellers set at an agitation speed of 70 rpm, 1.6 liters of liquid WP medium and 64 g (fresh weight) of the standard cells were transferred and cultured while feeding 1% $CO_2$-containing air at a speed of 0.05 vvm or 0.1 vvm in a dark at 25° C. for 14 days.

The cells were recovered from the resultant culture by vacuum filtration, and the entire volume was used in the subsequent main culture as seed cells.
(2) Main culture To a jar fermentor of the same type as described above, the seed cells and 1.5 liters of liquid WP medium containing 100 μM methyl jasmonate were added. Main culture was carried out while feeding the same gas as used in the preculture at a speed of 0.05 vvm. The other culture conditions and the culture period were the same as in the preculture.

The taxane-type diterpenes contained in the resultant cells and the medium were quantitatively determined in the same manner as described in Example 7. The $k_L a$ value for each of the aeration conditions was determined by the method as described previously. It should be noted here that the $k_L a$ in the preculture is higher than that in the main culture even under the same aeration speed because the volume of medium per jar fermentor is greater in the preculture to give a greater liquid depth (aeration speed: 0.05 vvm; $k_L a$ in the preculture: 22 $h^{-1}$; $k_L a$ in the main culture: 19 $h^{-1}$). The results are shown in Table 9.

COMPARATIVE EXAMPLE 2

The same operations as in Example 8 were carried out except that the speed of aeration to the jar fermentor in preculture was 0.02 vvm. The results are shown in Table 9.

TABLE 9

(After main culture)

| Aeration speed at preculture (vvm) | $k_L a$ ($h^{-1}$) | Cell yield (g/l) | Taxol (mg/l) | Baccatin III (mg/l) |
|---|---|---|---|---|
| 0.02 (Com. Example 2) | 8 | 21 | 10 | 2 |
| 0.05 (Example 8) | 22 | 29 | 51 | 8 |
| 0.1 (Example 8) | 36 | 38 | 184 | 19 |

As shown in Table 9, a remarkable effect of $k_L a$ in preculture was recognized upon the productivity of taxane-type diterpenes (yields of taxol and baccatin III) at the end of main culture, i.e., the productivity of taxane-type diterpenes was remarkably increased in Example 8.

It was unexpected that either $k_L a$ or DO does not influence the amount of cells obtained (cell yield) or the productivity of taxane-type diterpenes (yields of taxol and baccatin III) at the end of the preculture, but specifically influences the latent ability of cells to produce those diterpenes.

What is claimed is:

1. A method for producing a taxane ring containing alkaloid by culturing cells of a plant which produces taxane ring containing alkaloids, which comprises
    (1) conducting both of the following steps (a) and (b) so that the percentage of cell clusters having a mean diameter ranging from 0.12 mm to 1.6 mm becomes 65% or more of the gross fresh weight of the cells, wherein said mean diameter is calculated as the intermediate value between the major axis and the minor axis of said cell cluster:
        (a) conducting at least one operation for removing cell clusters other than cell clusters having a mean diameter ranging from 0.12 mm to 1.6 mm with a sieve and/or a filter having a pore size of 1410 μm or less:
            (i) during culturing at a $2^{nd}$ to $10^{th}$ culture prior to main culture for the production of a taxane ring containing alkaloid, and/or
            (ii) at the time of cell transfer carried out prior to each of said $2^{nd}$ to $10^{th}$ culture;
        (b) culturing the cells under an agitation speed of 30–180 rpm,
        wherein conducting both steps (a) and (b) results in a cell culture, wherein 65% or more of the gross fresh weight of cells in said resultant cell culture are cell clusters having a mean diameter ranging from 0.12 mm to 1.6 mm, and wherein said resultant cell culture is supplied to the main culture; and
    (2) recovering the taxane ring containing alkaloid from the resultant main culture.

2. The method of claim 1, wherein in said resultant cell culture the percentage of cell clusters having a mean diameter ranging from 0.12 mm to 1.0 mm is 80% or more relative to the gross fresh weight of the cells.

3. The method of claim 1, wherein in said resultant cell culture the percentage of cell clusters having a mean diameter ranging from 0.12 mm to 1.6 mm is 80% or more relative to the gross fresh weight of the cells.

4. The method of claim 1, wherein said taxane ring containing alkaloid is as least one selected from the group consisting of taxol, 10-deacetyltaxol, 7-epitaxol, baccatin III, 10-deacetylbaccatin III, 7-epibaccatin III, cephalomannine, 10-deacetylcephalomannine, 7-epicephalomannine, baccatin VI, taxane 1a, xylosyl cephalomannine, xylosyl taxol, taxol C, 10-deacetyltaxol C, taxisine I, taxisine II, taxine I, taxine II and taxagifine.

5. The method of claim 1, wherein the plant which produces taxane ring containing alkaloids is a plant belonging to the genus Taxus.

6. The method of claim 5, wherein the plant belonging to the genus Taxus is *Taxus media* or *Taxus baccata*.

7. The method of claim 1, wherein a jasmonic acid derivative or a coronatine derivative is used in the main culture as a promoting agent for the production of said taxane ring containing alkaloid, wherein said jasmonic acid derivative is at least one selected from the group consisting of jasmonic acids, alkyl esters of jasmonic acids, and imino- or amino-derivatives of jasmonic acids, and wherein said coronatine derivative is at least one selected from the group consisting of coronatine and coronafacic acid.

* * * * *